US006294678B1

(12) United States Patent
Sakalosky

(10) Patent No.: US 6,294,678 B1
(45) Date of Patent: Sep. 25, 2001

(54) TREATMENT FOR CANCER AND COMPOUNDS FOR USE THEREWITH

(76) Inventor: George P. Sakalosky, 410 Gatlin Dr., Gatlinburg, TN (US) 37738

( * ) Notice: Subject to any disclaimer, the term of this patent is extended or adjusted under 35 U.S.C. 154(b) by 0 days.

(21) Appl. No.: 09/005,996

(22) Filed: Jan. 12, 1998

Related U.S. Application Data

(60) Provisional application No. 60/035,101, filed on Jan. 14, 1997.

(51) Int. Cl.$^7$ ............................... C07F 3/00; C07F 3/06; C07F 9/94; C07F 19/00
(52) U.S. Cl. ............................ 549/210; 549/315
(58) Field of Search ....................... 349/210, 315

(56) References Cited

U.S. PATENT DOCUMENTS

| | | | |
|---|---|---|---|
| 2,259,492 | 10/1941 | Ruskin | 987/23 |
| 2,312,195 | 2/1943 | Ruskin | 514/184 |
| 2,400,171 | 5/1946 | Ruskin | 514/474 |
| 2,427,692 | 9/1947 | Ruskin | 514/184 |
| 5,639,787 | 6/1997 | Riordan et al. | 514/474 |

FOREIGN PATENT DOCUMENTS

| | | |
|---|---|---|
| 488784 | 7/1938 | (GB) . |
| 9528084 | 4/1995 | (WO) . |
| 9719949 | 11/1996 | (WO) . |

OTHER PUBLICATIONS

*The Predictor Model,* G. P. Sakalosky, Ph.D., A Grams Communications Publication, 1992.
"Sequence Analysis of Drosophila Histone Genes," Doctoral dissertation of Michale Lewis Goldberg, Apr. 1979.
"Proton Symmetry: Its Implications for Learning Theory—a Biophysical Concept," Doctoral dissertation of George P. Sakalosky, Apr. 8, 1975.

*Primary Examiner*—Richard L. Raymond
(74) *Attorney, Agent, or Firm*—Dorsey & Whitney LLP

(57) ABSTRACT

A treatment for cancer and compounds for use therewith are provided. The compounds treat cancer by correcting a TATA box lesion in DNA that leads to the cancer's uncontrolled cell proliferation. The preferred compounds each contain strontium; iodine; ascorbic acid; and a diamagnetic ion, either bismuth, zinc, or potassium. These components orient the compound, transport it to the lesion, dissociate the aberrational bonds of the lesion, hydrogenate the dissociated TATA nucleotides at the lesion, and reconvert the lesion's chemical structure to that of normal DNA.

5 Claims, 5 Drawing Sheets

Formula A

Formula B

Zinc Iodiscorbate

Potassium Iodiscorbate

TREATMENT FOR CANCER AND COMPOUNDS FOR USE THEREWITH

This application claims the benefit of U.S. provisional application Ser. No. 60/035,101, filed Jan. 14, 1997.

FIELD OF THE INVENTION

The present invention relates to cancer treatment. More particularly, it relates to a method for treating and curing cancer, and to compounds for use in the treatment. The present invention provides a totally new and unique approach to the identification of the primary carcinogenic lesion and site in DNA and to removal of the lesion and restoration of the site to achieve normal function.

BACKGROUND OF THE INVENTION

A cancer is a malignant tumor of potentially unlimited growth. It is primarily the pathogenic replication (a loss of normal regulatory control) of various given types of cells found in the human body. By select mutation resulting from a primary lesion, the DNA of a cancer cell evolves and converts the cell into an autonomous system. Conventional cancer treatments have focused mainly on killing cancerous cells. Such treatments threaten noncancerous cells, inherently are stressful to the human body, produce many side effects, and are of uncertain efficacy. More important, such treatment regimens are not ordinarily directed toward the actual chemical bond root of the cancer problem.

Cancer cells possess uncontrolled replication. Such uncontrolled replication readily can be caused by a chemical bond lesion in the cell's deoxyribonucleic acid (DNA). Specifically, certain chemical and radiation energy sources can cause chemical bond alterations in DNA. These alterations can and do result in production of photoproducts and chemical energy products in various parts of the genome. One such product, called an ozonide, has the catalytic properties to continuously activate cell replication, to produce mutations within the genome, and to replicate itself by autoxidation. References 1–4. This catalytic lesion in the nucleotide sequence responsible for activating the oncogene is identified herein as the primary carcinogenic lesion, and has served as the basis of the design of the compounds of the present invention. As yet, no compounds, other than those presented herein, have been designed or used specifically to dissociate the chemical bonds of an ozonide in DNA, nor are any treatment methods available that are directed toward correcting this chemical bond aberration to DNA replication, i.e., for eliminating the primary carcinogenic lesion in DNA.

There is an unmet need for a therapeutic regimen for cancer, one that is based on removing a critical lesion in one of DNA's regulatory structures and thus normalizing DNA replication and returning the regulatory system to its normal state whereby it can activate apoptosis (cell suicide). There further is an unmet need for compounds designed to be effective in such a treatment regimen. There also is an unmet need for a treatment regimen and associated compounds that are not toxic to the patient, but that instead simply eliminate the primary carcinogenic lesion and correct the regulatory aberration.

SUMMARY OF THE INVENTION

The present invention relates to a method for cancer treatment and to compounds for use in that treatment. The present invention focuses on the uncontrolled replication of DNA, the primary lesion initiating carcinogenesis, and the TATA box in DNA. The TATA box (so named for its base pair sequence of Thymine-adenine, Adenine-thymine, Thymine-adenine, Adenine-thymine) is located at the beginning of a DNA promoter (a promoter is a section of DNA that directs the binding of ribonucleic acid (RNA) polymerase to initiate transcription). Reference no. 5. The TATA box protein (TBP) activates the box and thus the promoter by bending the box and providing the appropriate cofactors to initiate transcription. References no. 3 and 4. The TATA box functions as a regulatory unit —an on-off switch—for DNA transcription and (via transcription) replication. The on-off switch in the TATA box is a function of the movement of the hydrogen ion between a thymine oxygen and an adenine nitrogen in the TATA box.

DNA transcription is activated when the TATA box is contacted and straddled by the TBP to form a TBP/TATA box complex. Reference no. 6. When the TBP straddles the TATA box, it bends the TATA box at an angle of 100° along the DNA axis. Reference no. 7. The TBP-induced bend initially breaks the oxygen-based hydrogen bond between the first of the complimentary adenine-thymine pairs in the TATA box, and in so doing creates within that thymine nucleoside a second oxygen double bond (prior to the bending, only one oxygen double bond existed in the thymine nucleoside). When the TATA box is bent by the TBP, these two oxygen double bonds are moved into close proximity to one another. If energy impacts these two momentarily associated oxygen double bonds, an energy process which attacks a nearby carbon-carbon double bond, a covalent-bonded ozonide is produced. Reference no. 2.

The ozonide thus consists of the nucleoside's three oxygens and the two carbons from the thymine nucleoside's 5–6 double bond. The ozonide eliminates the possibility of hydrogen bond formation with the thymine oxygen atom (which is now bound within the ozonide) to turn the system "off." The ozonide in the regulatory replication-initiation TATA sequence of the DNA oncogene thus locks the TATA system in the "on" (transcription/replication) state, forming the basis for the malignancy. It is to be noted that the Law of Bergonie and Tribondeau, published in 1906, states that a tissue is more radiation-sensitive (and can become cancerous) the more undifferentiated its cells are morphologically and physiologically, the more active they are mitotically, and the longer they remain in an active state of proliferation (the more divisions they undergo between the youngest precursor cell and the mature functional cell). The bending of the TATA box during such active proliferation momentarily provides open windows for energy absorption and lesion production in the momentarily associated oxygen double bonds within the TATA box. Reference no. 4. This is the primary mechanism responsible for the genesis of cancer, and the ozonide is thus the primary lesion responsible for carcinogenesis. All mutations in the genome resulting from this lesion and from other sources are considered secondary effects in the cancer process. However, many of these mutations are essential to the evolution of an operational and autonomous cancer cell.

The ozonide is highly diamagnetic due to the coupling and pairing of all of its electrons (diamagnetism is exhibited by elements possessing an even number of electrons and no incomplete inner shells). All effective ozonide orbitals are filled continuously by paired pi and lone electrons from structures surrounding the lesion and correspond to the electron configuration of krypton (this is the Sidgwick effective atomic number process). Reference no. 8.

The ozonide has known physicochemical autoxidation properties, which enable the ozonide to self-replicate. When the ozonide is produced in one thymine nucleoside during the DNA replication process, it immediately can replicate itself, by autoxidation, in an associated thymine nucleoside. Thus, the structure of the TATA box permits replication of the ozonide from the thymine in the DNA mother strand to the thymine in the adjacent daughter strand, thereby permitting, during normal strand separation, during replication, the transfer of the ozonide lesion from one cell to another.

The present invention is based on compounds that are designed to address and dissociate the covalent bonds of the ozonide lesion in the TATA box of the oncogene. Each of the compounds contains a constituent that orients the compound toward, and transports it to, the TATA lesion in the DNA. Each compound also has constituents that dissociate the ozonide's bonds, and hydrogenate the nucleotide-linking oxygen in the thymine nucleoside. The constituents of the compounds have been highly selected, and the compounds designed specifically, to reconvert the carcinogenic chemical structure of the thymine nucleoside to that found in normal DNA. The preferred compounds applicable for this purpose include the primary compound, bismuth iodiscorbate, and two analogs, zinc iodiscorbate and potassium iodiscorbate.

A primary object of the present invention is to provide a treatment regimen and compounds for use therewith directed toward dissociating the covalent bonds of the DNA's TATA-box ozonide, and thus deactivating this regulatory nucleotide sequence to obtain a cancer-therapeutic effect. Another object of the present invention is to provide a treatment regimen and associated compounds that are not toxic to the patient.

These and other objects of the present invention will become apparent with reference to the description of the preferred embodiment.

DETAILED DESCRIPTION OF THE PREFERRED EMBODIMENT

Figure 1:
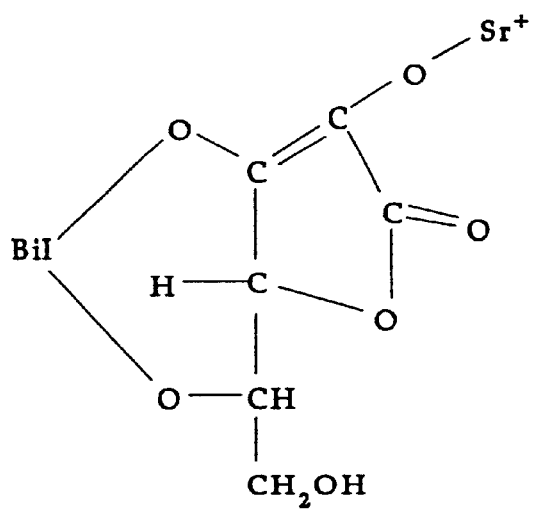
FIG. 1 depicts a chemical compound, Bismuth Iodiscorbate, hereinafter referred to as Formula A.

The present invention is directed toward (1) compounds designed to eradicate the ozonide and return the TATA box to its normal functioning state in order to initiate a cancer-therapeutic effect, and (2) to identifying methods for using these compounds. The preferred compounds feature iodine bonded to a stabilized metal salt (such as bismuth, zinc, or potassium) which is bonded to strontium and an organic acid (ascorbic acid). Thus, each of the preferred compounds has four components: a diamagnetic ion (such as bismuth, zinc, or potassium), iodine, strontium, and ascorbic acid. The diamagnetic ion (bismuth being the most diamagnetic of all the diamagnetic elements) serves to direct the compound to the highly activated diamagnetic lesion. The strontium and ascorbic acid serve together to hydrogenate the TA nucleotide-binding thymine oxygen, and thus link the thymine and adenine nucleotides. The iodine is the primary element of the compound, in that its function is to dissociate the covalent bonds of the ozonide.

Because the TATA-box ozonide provides a powerful diamagnetic site, the compound necessarily must contain a diamagnetic metal ion in order for the compound to coordinate with the site. Thus, the purpose of the diamagnetic ion is to orient the compound and to carry it directly to the specific TATA lesion in the DNA. In addition, the generally paramagnetic fields that surround normal DNA would tend to repel the diamagnetic ion and move it toward and onto the diamagnetic lesion, which would, of course, attract the diamagnetic ion (a pull/push effect). Because the diamagnetic ion is attracted only to the lesion, a highly activated and diamagnetic site, it should not affect normally activated promoter sites. Accordingly, once the aberrated site is deactivated by the compound and thus loses it diamagnetic properties, the compound automatically would be repelled from the site and from the cell.

The compound's diamagnetic ion preferably is either bismuth, zinc, or potassium. Bismuth in the primary compound is the most preferred because it is the most diamagnetic of all the diamagnetic elements. However, the diamagnetic properties of the analogs, zinc and potassium, also are capable of a similar function and may perform more effectively than the primary compound. In addition, it is contemplated that other elements that can substitute for the element bismuth in the compound, such as sodium or phosphorus, also are within the scope of the present invention.

The primary compound and its analogs all contain iodine. Iodine is an important and active constituent to dissociate ozone. Once the compound reaches the highly activated, diamagnetic site, the iodine will split the ozonide's covalent bonds. It will do so by catalytically dissociating the oxygen elements of the ozonide, thus reconverting the ozonide structure to the normal thymine structure in the DNA. By dissociating the ozonide's chemical bonds, the iodine removes the primary carcinogenic lesion. Other halides also may be suitable for this purpose.

As described, the preferred compounds contain strontium and ascorbic acid. These two components participate in hydrogenation of the unbonded oxygen that normally is part of the bond between the oxygen and the nitrogen of the complementary thymine-adenine pair. This reforms the hydrogen bond at the unbonded site and, as a result, turns off the activated TATA box.

The preparation of the preferred compounds now will be described. There are many methods for synthesizing the compounds of the present invention. Each is acceptable and within the scope of the present invention. The bismuth compound may be prepared from SrI, bismuth, and D- or L-ascorbic acid in mole ratios of 1:1. The ascorbic acid is dissolved in glycerol ($CHOH(CH_2OH)_2$) to distribute the ascorbic acid molecules symmetrically, thus exposing the ascorbic acid's reactive hydroxyl sites. SrI, a subhalide of strontium, then is added in an amount that is not sufficient to neutralize the acid. Next, an aqueous solution of $Bi(NO_3)_3$ is added in an amount that is approximately equivalent to that of the ascorbic acid. Additional SrI then is added to raise the pH above 8.0. Finally, ascorbic acid is added to lower the solution's pH to a level acceptable for therapeutic use.

The compound depicted as Formula A (FIG. 1) has the formula $BiISrC_6H_5O_6$, and may be produced by performing the above-described process at a temperature of about 25° C. By way of specific example, the compound may be produced as follows: Equal molar quantities of D- or L- ascorbic acid, SrI, and $Bi(NO_3)_3$ are added at a temperature of 25° C. First, 176 g of ascorbic acid are dissolved in 500 ml of glycerol. Next, 100 g of SrI (an amount insufficient to neutralize the acid) is added while the solution is stirred and cooled to 25° C. Next, 20% increments of 500 ml aqueous solution containing 395 g of $Bi(NO_3)_3$ are added alternately with 20% increments of 114 g of SrI while the solution is stirred and maintained at a temperature of 25° C. An orange salt will precipitate out of the solution. This precipitate is centrifuged and washed several times with distilled water by centrifugation. Next, 5 g of the moist precipitate is suspended in 100 ml of 50% glycol. If the solution is cloudy, it may be filtered, and a stabilizing solution of 2.5 cc $Na_2SO_3$ solution (containing 250 mg $Na_2SO_3$) may be added. The compound is rendered suitable for therapeutic use by adding additional ascorbic acid to lower the pH to about 7.6. The compound that is produced by this method may be water soluble or insoluble.

Figure 2:
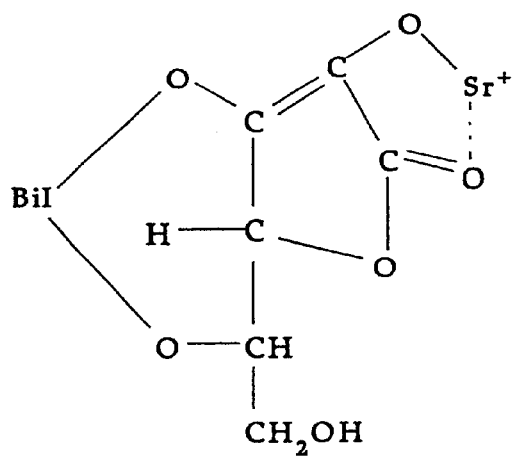
FIG. 2 depicts a second chemical compound, Bismuth lodiscorbate, hereinafter referred to as Formula B.

The compound depicted as Formula B (FIG. 2) has the formula $BiISrC_6H_5O_6$ and has a stereochemical conformation (i.e., the intermolecular hydrogen bond and its ionic association with the univalent strontium are in mobile equilibrium). Formula B is prepared in the same manner as is Formula A, except upon the initial addition of SrI the solution is rapidly cooled to and maintained at 15° C.

It is to be noted that SrI is a subhalide of strontium, and is obtained from the free metal and the normal halide by heating $SrI_2$ and strontium to a temperature of at least 780° C. This melt is chilled quickly to room temperature to avoid the possibility of reversion at the intermediate temperatures. It is to be noted that the subhalide, SrI, decomposes in time under normal conditions into the free metal and the normal halide. SrI is an intense brown, well-crystallized, and hygroscopic. When decomposed, SrI forms $Sr(OH)_2$ and ordinary halide. The bismuth should be used in the form of bismuth nitrate. The nitrate acts as a catalyst and as an oxidizing agent to enhance direct iodination, resulting in the compound's iodination product.

Figure 3:
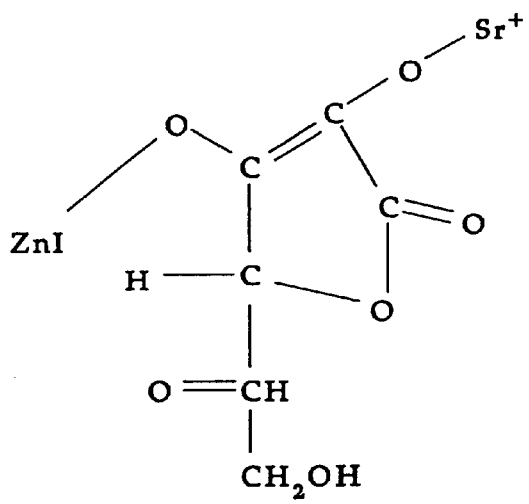
FIG. 3 depicts a third chemical compound, Zinc Iodiscorbate.
Figure 4:
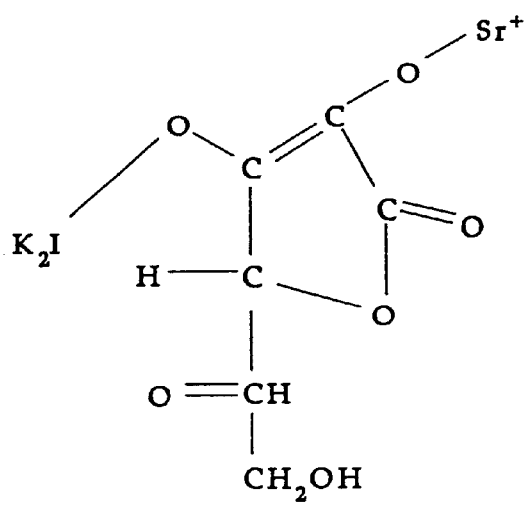
FIG. 4 depicts a fourth chemical compound, Potassium Iodiscorbate.

ZnSrI ascorbate, entitled zinc iodiscorbate, may be synthesized as follows: Zinc oxide and strontium hydroxide are added in 1:1 molar concentrations to deionized water. Hydriodic acid (1 mole, 57 weight percent) is stirred in (a suspension still will be present after several hours). Ascorbic acid (3 moles) is added; this dissolves the suspension, resulting in a clear solution. The water is removed under vacuum at a temperature of approximately 25° C., leaving behind a crystalline solid. The empirical formula for the zinc iodiscorbate is $ZnSrI(ascorbate)_3$. The potassium iodiscorbate is synthesized in a similar manner, substituting potassium for zinc (refer to FIGS. 3 and 4). This compound produced by this method also may be water soluble or insoluble. For the compounds of the present invention, solubility in water is preferred because the compounds may be easier to work with.

The following are additional and more simplified methods for synthesizing the three preferred compounds:

Bismuth Iodiscorbate

Bismuth iodiscorbate was prepared by dissolving 58 g of concentrated hydriodic acid (56.1 weight-percent) into 350 mls of water. Next, 5 g of 0.0085 molar bismuth (III) iodide was crushed in a mortar, and then dissolved in the solution. Next, 2.3 g of 0.0085 molar strontium hydroxide octahydrate was stirred into the solution, followed by the addition of 4.5 g of 0.026 molar L-ascorbic acid. The mixture was stirred for three hours, then stripped to dryness on a rotary evaporator. The residue then was redissolved in 500 ml water and filtered, and again stripped on a rotary evaporator. This process assisted in the removal of excess hydriodic acid. The residue again was dissolved in 500 ml of water, filtered, and stripped to dryness on a rotary evaporator. An orange solid then was removed from the flask and bottled. This procedure yielded 9.1 g of what is designated as $SrBiI_2[ascorbate]_3$. This compound was water soluble.

Potassium Iodiscorbate

Potassium iodiscorbate was prepared by adding 6.5 g of 0.12 molar potassium hydroxide and 16.0 g of 0.06 molar strontium hydroxide octahydrate to 500 ml water in a 1000-ml beaker, resulting in a white, cloudy solution. The mixture was stirred for about 2 hours. Next, 13.0 g of 0.06 molar hydriodic acid (56 weight-percent) was added, and the mixture was stirred for three hours. Next, 3.2 g of 0.18 molar L-ascorbic acid was added, turning the mixture clear in about 5 minutes. The mixture then was stirred for another 0.5 hour. The water was removed under vacuo, and the residue dried under vacuum for about 8 hours. The solids were removed from the flask and bottles. The structure is designated as $[ascorbate]_2SrK[ascorbate]KI$. This compound also was water soluble.

Zinc Iodiscorbate

Zinc iodiscorbate was prepared by adding 4.0 g of 0.05 molar zinc oxide and 13.3 g of 0.05 molar strontium hydroxide octahydrate to 500 ml of distilled water, resulting in a white suspension. The mixture then was treated with 11.2 g of 0.05 molar concentrated hydriodic acid and stirred for two hours. A white suspension still remained. Next, 26.4 g of 0.15 molar L-ascorbic acid was added, and the reaction mixture became colorless within 20 minutes. The solution was evaporated to dryness on a rotary evaporator, then dried under vacuo for 8 hours at room temperature. The resulting yellow-orange powder was transferred to a tarred bottle. The structure of this compound was designated $[ascorbate]_2SrZn[ascorbate]I$. This compound also was water soluble.

For therapeutic application, the compound may be encapsulated with a liposomal (or other carrier) structure and delivered to and into the cancer cell by various methods. Suitable methods include subcutaneous, intravenous, and intraperitoneal delivery. Accordingly, the method aspect of the present invention includes the following steps: First, the cancerous tissue must be identified. Next, the appropriate delivery method must be selected; this will depend on the nature of the cancerous tissue. The compound next is delivered to the tissue, as follows: The compound is introduced into the cell and thus into the targeted region, thus permitting the diamagnetic ion to orient the compound and carry it directly to the diamagnetic TATA lesion. Once the compound reaches the lesion, the ozonide's covalent bonds are split, and the ozonide structure is dissociated. The thymine oxygen is hydrogenated by the compound's strontium and ascorbic acid; the hydrogen then links the thymine and adenine nucleotides by reforming a hydrogen bond at the unbonded site and turning off the highly activated TATA box.

Three compounds of the present invention, specifically, bismuth iodiscorbate, potassium iodiscorbate, and zinc iodiscorbate, were tested in vitro on both tumorous and normal human cells. Three cell lines were obtained through the American Type Culture Collection (Rockville, Md.). The first cell line, designated HUV-EC-C, consisted of human umbilical cord vein normal endothelial cells. These noncancerous cells were used as a control. The second cell line, MCF-7, consisted of breast carcinoma cells. The third cell line, ME-180, consisted of uterine cervix carcinoma cells.

Figure 5:
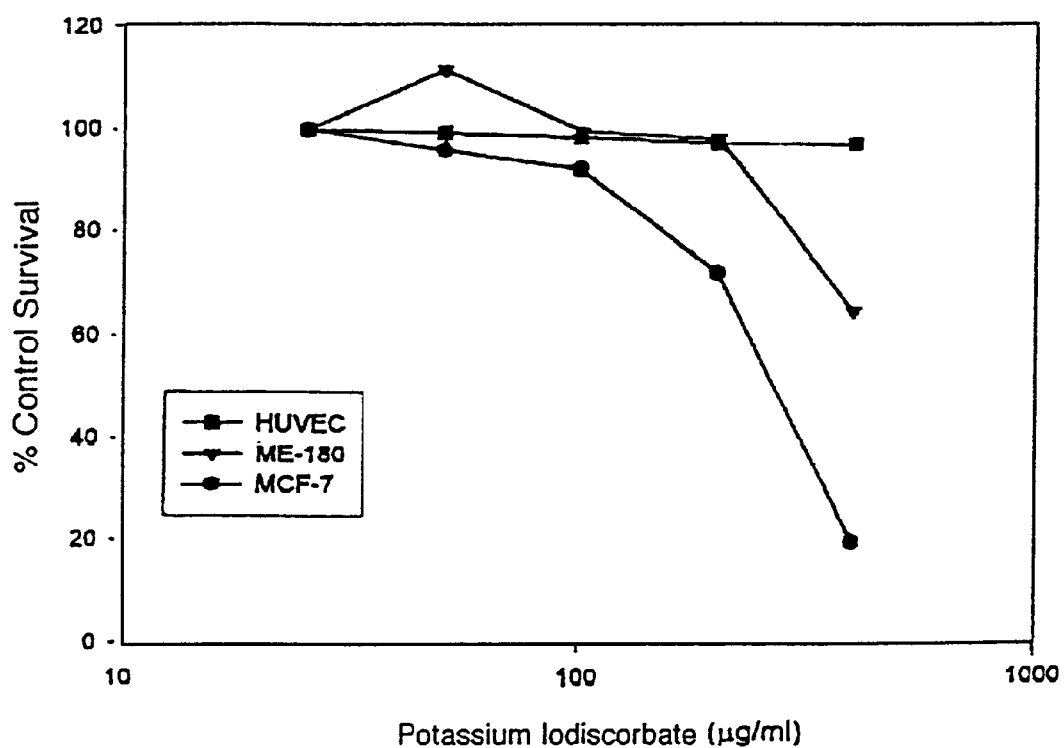
FIG. 5 is a graph depicting the effect of Potassium Iodiscorbate on tumor and normal cell growth.

Potassium iodiscorbate was effective in reducing dramatically the survival of breast carcinoma cells (MCF-7) at concentrations greater than 100 μg/ml. This compound did not affect the growth of normal human endothelial cells (HUV-EC-C) at any concentration tested. The compound also reduced dramatically the survival of human cervical carcinoma cells (ME-180). When cells at high density (near confluence in culture dishes) were treated with the potassium compound at 400 μg/ml, the compound had little effect, suggesting that cells must be actively dividing to be affected by this agent. This suggests that the compound targets cycling cells and induces apoptosis at specific phases of the cell cycle. FIG. 5 depicts percent cell survival against various concentrations of potassium iodiscorbate.

Figure 6:
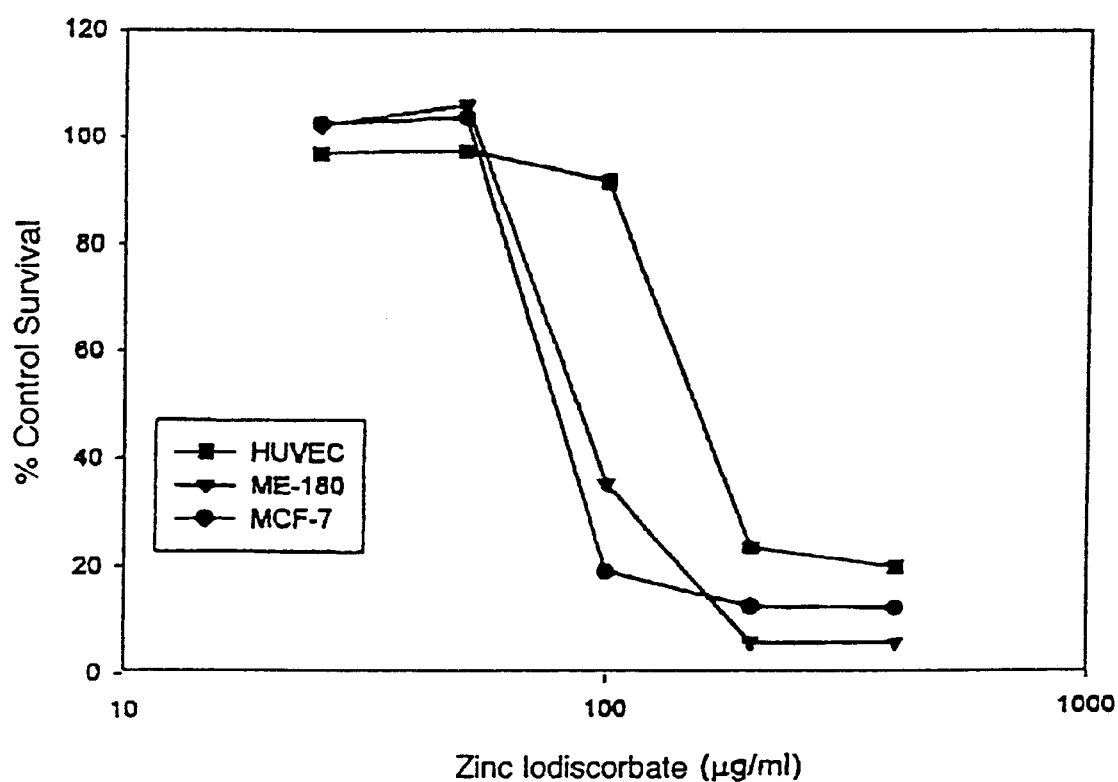
FIG. 6 is a graph depicting the effect of Zinc Iodiscorbate on tumor and normal cell growth.

At about 80–100 μg/ml, zinc iodiscorbate reduced the growth of all cell lines tested without serious reduction of normal cell growth. At that dose level, the survival of both cancer cell types was reduced dramatically with respect to normal cell growth. Thus, the zinc iodiscorbate can reduce survival of those tumor cells at intermediate concentrations. FIG. 6 depicts percent cell survival against various concentrations of zinc iodiscorbate.

Figure 7:
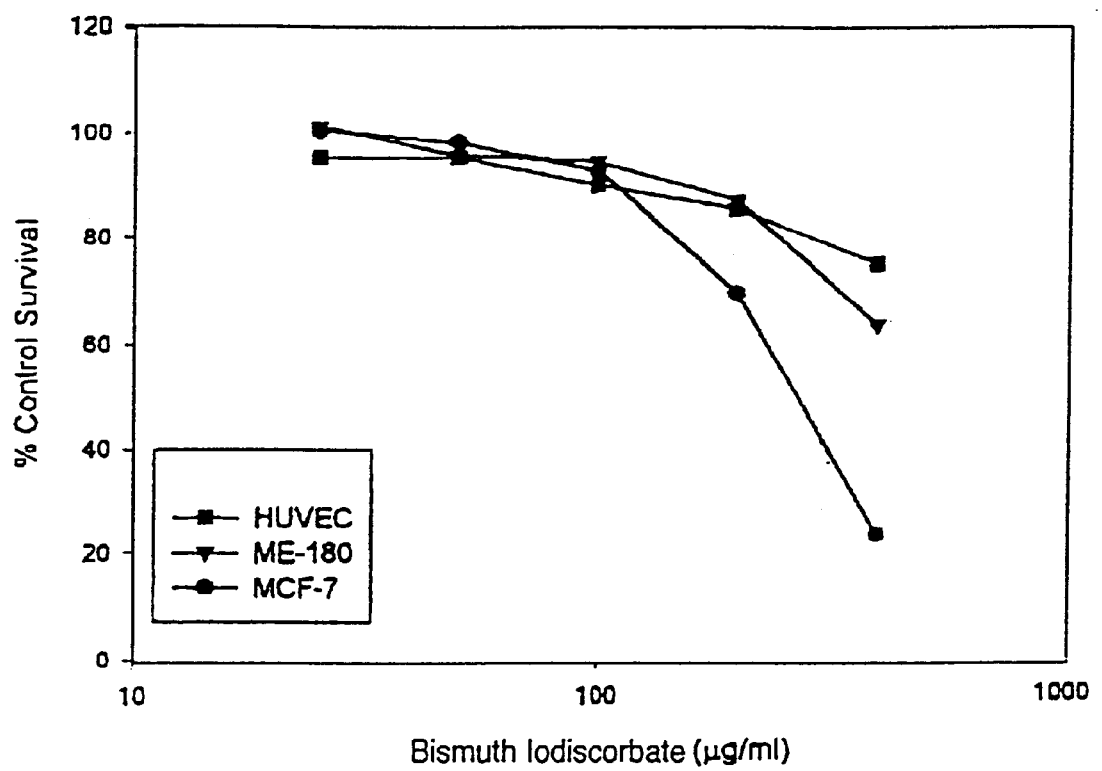
FIG. 7 is a graph depicting the effect of Bismuth lodiscorbate on tumor and normal cell growth.

Bismuth odiscorbate produced results very similar to those of potassium iodiscorbate, and was effective in reducing the survival of both human breast cancer (MCF-7) and human cervical cancer cells (ME-180). FIG. 7 depicts percent cell survival against various concentrations of bismuth iodiscorbate.

The data shown in FIGS. 5–7 were derived by the following steps. HUV-EC-C was cultured in a solution of 90% F12 medium (GIBCO-BRL, Grand Island, N.Y.) and 10% fetal bovine serum (Hyclone, Logan, Utah) with 100 μg/ml heparin and 30 μg/ml ECGF (endothelial cell growth factor; Sigma Chemical Co., St. Louis, Mo.). MCF-7 and ME-180 were grown in a solution of 90% minimal essential medium (GIBCO-BRL) and 10% fetal bovine serum (Hyclone). The cells were grown to approximately 90% confluence in T25 cell culture flasks (Falcon-Becton Dickinson Labware, Franklin Lakes, N.J.) in a 37° C. humidified incubator in the presence of 5% $CO_2$-95% air.

Flasks were removed from the incubator and placed in a sterile laminar flow hood. All cell manipulation procedures were performed in this sterile hood. The flasks were rinsed in 5 ml of sterile phosphate-buffered saline (PBS; Sigma) and the monolayer of cells was released from the flask by adding 5 ml of 1× trypsin-EDTA (Sigma) in PBS. The flask was capped and placed back in the incubator for 10 minutes. The flasks were removed from the incubator, and cells plus trypsin-EDTA solution were transferred to a 15 ml centrifuge tube (Falcon) and 5 ml of cell growth medium was added. The tubes were centrifuged at 500 g for 10 minutes at room temperature. The tubes then were placed back in the hood and supernatant (top liquid) was removed with a sterile pipette (Falcon). The cells (at the bottom of the centrifuge tube) were resuspended in 5 ml of their growth media and a small aliquot (0.1 ml) was removed and placed in a hemacytometer. The cell density in the hemacytometer was determined by counting cells visible by microscopy. The cells in the original centrifuge tube were diluted to a cell concentration of 60,000 cells per ml of growth media. One hundred μl aliquots of each of these cell suspensions were transferred to individual wells of a 96-well culture plate (20 wells used for each cell line). The cell culture plates were placed into the incubator for 18 hours.

Because each compound contains iodine, the potassium, bismuth, and zinc iodiscorbate compounds were weighed out on a microbalance in subdued lighting (no direct light except that filtering in from windows). The compounds were transferred directly to glass test tubes and sufficient triply-distilled water was added to each tube to achieve a final concentration of 40 mg/ml of compound in water. These solutions were diluted fifty-fold into cell growth medium for a final concentration of 800 μg/ml in medium used for the different cell lines. A portion of this solution was diluted with an equal volume of cell growth medium for a concentration of 400 μg/ml. A portion of this solution (400 μg/ml) was diluted with an equal volume of media to achieve a concentration of 200 μg/ml. This dilution procedure was repeated until the concentration of compound in media was 1.5625 μg/ml.

One hundred μl aliquots of the 10 resultant solutions of diluted compound in cell growth media for HUVEC or MCF-7 cells were then added to wells of the 96 well plate containing cells with 100 μl of their respective growth media. Cell growth medium alone (100 μl) also was added to wells containing cells in the 96-well plate to be used as a control for cell growth in the absence of compound. The plates were incubated for 48 hours at 37° C. in the presence of compound in medium (as discussed above) or medium alone.

The medium in the cell culture plates then was removed by inverting the plate onto several layers of paper towels. One hundred μl of crystal violet dye solution (0.5% crystal violet (weight/volume) in 20% methanol, 80% water) was added to each well of the 96-well plate and incubated at room temperature for 20 minutes. The plates were rinsed 5 times by submersion in several 2-liter beakers full of water. The final rinse was done with distilled/deionized water. All water was removed from the wells by lightly tapping the plate on several layers of paper towel. The plates were then air-dried overnight.

One hundred μl of Sorenson's buffer (0.1 molar sodium citrate buffer, pH 4.2 in 50% ethanol, 50% water) then was added to each well and was incubated at room temperature for 6 hours with gentle mixing on a mixing platform. Light absorbance (color) at a wave length of 590 nanometers in each well of the 96-well plate was determined by placing the plate in an automated microplate reader (Bio-Tek Instruments Model #309, Winooski, Vt.). Absorbance values obtained from wells that received medium alone were used to give a relative absorbance associated with 100% cell survival. The effect of compound on the survival of cells was determined for each cell line using the formula outlined below:

$$\% \text{ cell survival} = (100) \frac{\text{absorbance of compound treated cells}}{\text{absorbance of medium alone treated cells}}$$

Percent cell survival was plotted for each cell line against compound concentration, as shown in FIGS. 5–7.

A toxicology study also was performed. Specifically, the toxicology of potassium iodiscorbate was evaluated through in vivo tests on mice. Potassium iodiscorbate was prepared as a stock solution of 175 mg/ml in saline and administered to mice. Injections consisted of a volume not exceeding 0.1 ml administered through the tail vein (intravenously), or a volume not exceeding 0.2 ml (by an intraperitoneal route). Doses up to 1000 mg/kg (intraperitoneal injection) and 500 mg/kg (intravenous injection) caused no apparent toxicity. This dose should permit use of the compounds of the present invention in concentrations (refer to FIGS. 5–7) that approximate those necessary for selective inhibition of malignant cell growth.

Although the description of the preferred embodiment has been presented, it is contemplated that various changes may be made without deviating from the spirit of the present invention. Accordingly, it is intended that the scope of the present invention not be limited strictly to that of the description of the preferred embodiment of the present invention.

References

Reference no. 1: George P. Sakalosky, Proton Symmetry: Its Implications for Learning Theory, A Biophysics Concept (1975) (Ph. D. thesis, Boston College (an interdisciplinary/intercollegiate Doctoral Thesis Program at Boston College, M.I.T., Tufts University School of Medicine, and Boston University)).

Reference no. 2: George P. Sakalosky, Ph. D., The Predictor Model (Grams Communications Publications, 1992).

Reference no. 3: George P. Sakalosky, Ph. D., Linking the TATA Box in DNA with Carcinogenesis via Molecular Modeling, Presentation at a Special Conference sponsored by the American Association for Cancer Research, "Transitional Research in Cancer: New Opportunities for Progress," (Nov. 29 through Dec. 4, 1994) (transcript available from Alchemy International, 101 N. Jay St., Middleburg, Va. 20118)).

Reference no. 4: George P. Sakalosky, Ph. D., and A. P. Jacobson, Ph. D., Submolecular DNA Radiation and the Genesis of Cancer (RIMI Publications, 1982).

Reference no. 5: Michael Lewis Goldberg, Sequence Analysis of Drosophila Histone Genes (1979) (Ph. D. thesis, Stanford University).

Reference no. 6: Youngchang Kim et al., Crystal Structure of a yeast TBP/TATA-box complex, Nature, Oct. 7, 1993, at 512.

Reference no. 7: Joseph L. Kim et al., Co-crystal structure of TBP recognizing the minor groove of a TATA element, Nature, Oct. 7, 1993, at 520.

Reference no. 8: Nevil Vincent Sidgwick, The Electronic Theory of Valency at Chapter X (Cornell University Press, 1927).

I claim:

1. A compound comprising a structure having the formula $XISrC_6H_5O_6$, wherein X is selected from the group consisting of bismuth, potassium, and zinc.

2. The compound of claim 1 wherein the structure has the formula $BiISrC_6H_5O_6$.

3. The compound of claim 1 wherein the structure has the formula $K_2ISrC6H_5O_6$.

4. The compound of claim 1 wherein the structure has the formula $ZnISrC_6H_5O_6$.

5. A compound consisting essentially of operably bonded iodine, ascorbic acid, strontium, and one member selected from the group consisting of bismuth, potassium, and zinc.

* * * * *